United States Patent [19]

Sciortino et al.

[11] 4,306,662
[45] Dec. 22, 1981

[54] INTRAVENOUS BOTTLE HOLDER

[75] Inventors: Vincent J. Sciortino, Des Plaines; Peter Smigura, Gurnee, both of Ill.

[73] Assignee: Heinz Plastic Mold Co., Elk Grove Village, Ill.

[21] Appl. No.: 187,961

[22] Filed: Sep. 17, 1980

[51] Int. Cl.³ .......................................... B65D 25/22
[52] U.S. Cl. .............................. 215/100 A; 248/318; 248/359; 294/27 R
[58] Field of Search ............... 215/100 R, 100 A; 294/27 H, 27 R, 31.2; 248/318, 311.3, 359

[56] References Cited

U.S. PATENT DOCUMENTS 3,220,591 11/1965 Hidding ........................ 215/100 A
3,635,367 1/1972 Morita et al. ................. 215/100 A
3,807,679 4/1974 Burke et al. ................ 215/100 A X
4,168,783 9/1979 Gargione ....................... 215/100 R Primary Examiner—Donald F. Norton
Attorney, Agent, or Firm—Jakala, Knechtel, Valentino, Demeur & Dallas

[57] ABSTRACT

An inexpensive bottle holder that can be removably attached to a bottle such as an intravenous bottle to support the bottle in an inverted position. The bottle holder has a hanger which normally is stored in a cavity formed beneath the top wall of the holder and the bottom of the bottle when the bottle is seated in an upright position, and which is automatically formed and ready for use when the bottle is picked up.

7 Claims, 4 Drawing Figures

U.S. Patent  Dec. 22, 1981  4,306,662
FIG. 1
FIG. 2
FIG. 3
FIG. 4
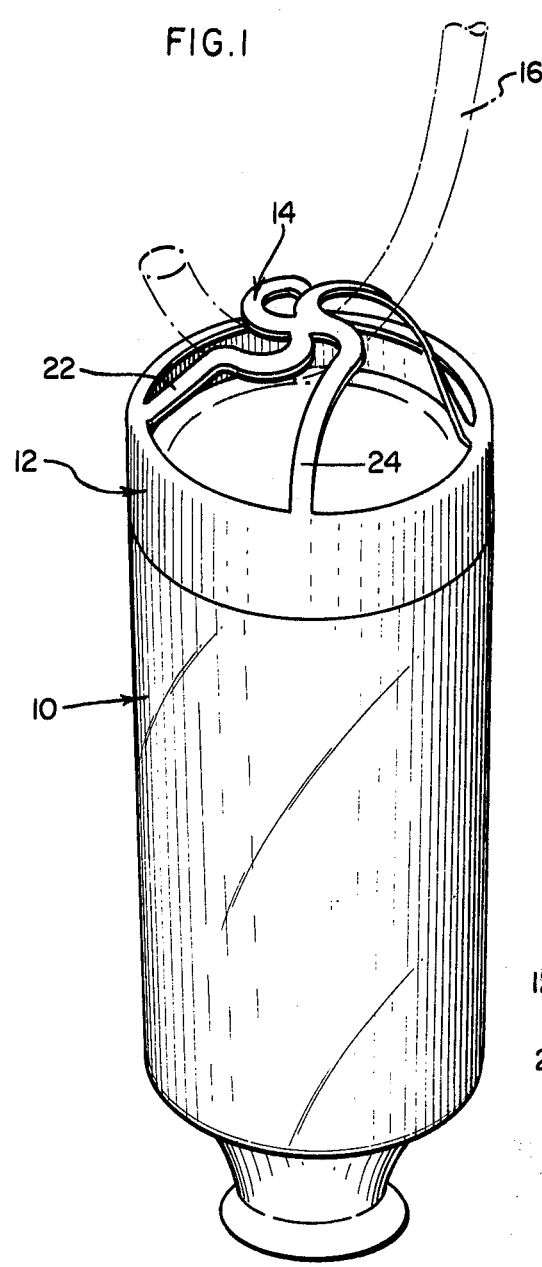
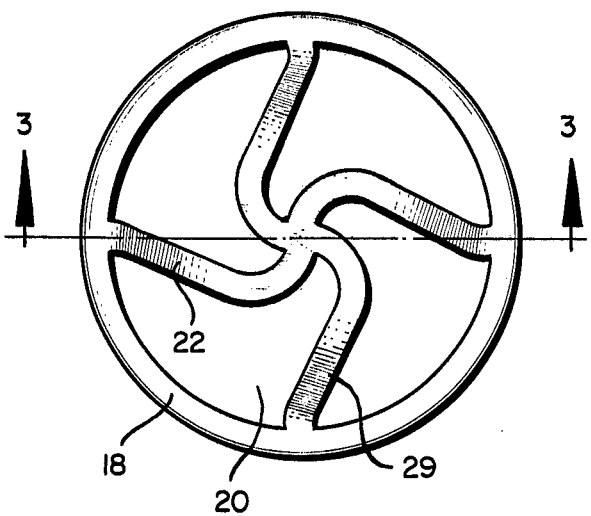
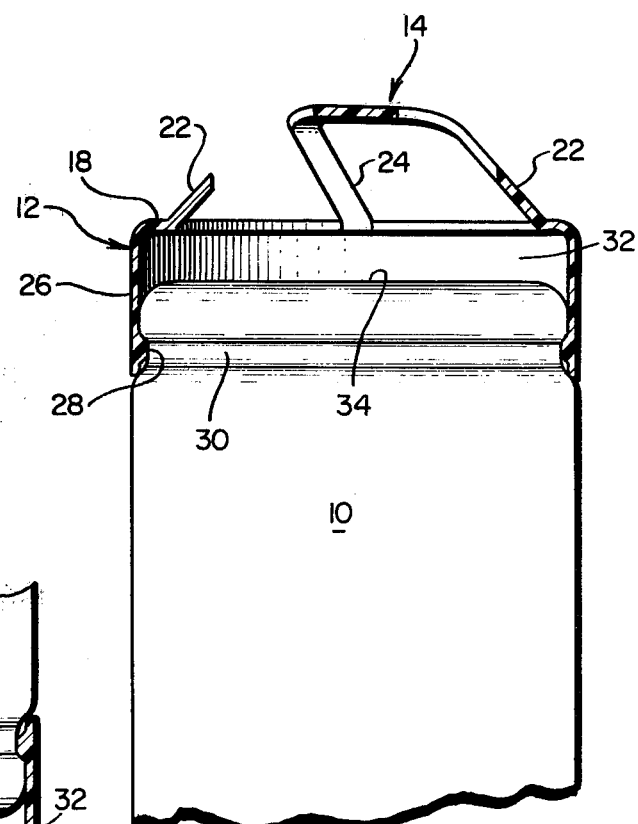
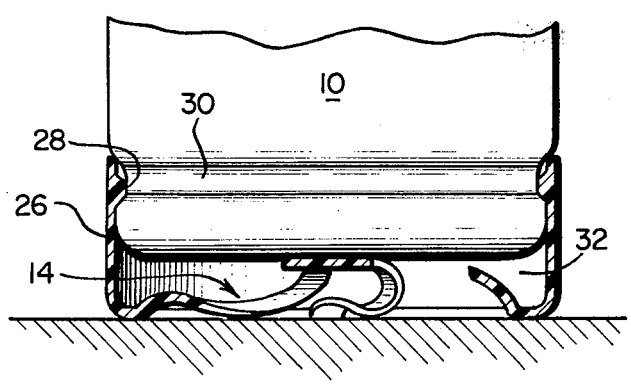

INTRAVENOUS BOTTLE HOLDER

BACKGROUND OF THE INVENTION

This invention relates to a bottle holder for hanging a bottle such as an intravenous bottle in an inverted position during its use.

Various bottle holders of the described type presently are available. One such bottle holder is disclosed in U.S. Pat. No. 4,168,783, and comprises a pleated bail which is expanded by grasping its opposite side edges and pulling it outwardly to provide a hanger which is then used to hang the bottle in an inverted position. The bottle holder per se is removably attached to the bottle. Other available bottle holders are of a similar construction.

One disadvantage of these bottle holders is that the "hanger" must be pulled or otherwise formed before the bottle can be suspended in an inverted position, thus both hands normally are required to hang the bottle. In many situations, the fact that both hands are required to hang the bottle makes it very cumbersome, difficult and awkward to form the hanger.

Accordingly, it is an object of the present invention to provide an inexpensive bottle holder that can be removably attached to a bottle such as an intravenous bottle to support the bottle in an inverted position. The bottle holder has a hanger which normally is stored in a cavity formed beneath the top wall of the holder and the bottom of the bottle when the bottle is seated in an upright position, and which is automatically formed and ready for use when the bottle is picked up.

SUMMARY OF THE INVENTION

These and other objects are provided by the bottle holder of the present invention which is integrally molded of a thermoplastic material having an elastic memory and has a top wall with an opening in it and a skirt portion depending from one side of the top wall. The skirt portion preferably is provided with an annular bead on its interior peripheral side wall that is proportioned to seat within an annular recess normally formed in the peripheral wall of intravenous bottles to removably affix the holder to the bottle. This annular bead also is positioned so that the top wall of the holder is spaced from the bottom of the bottle so as to provide an open cavity between the top wall of the holder and the bottom of the bottle when the holder is affixed to the bottle. A hanger is integrally formed with the top wall of the holder and spans the opening therein. The hanger essentially is formed by two generally S-shaped arms each of which is substantially longer in length than the diameter of the opening in the top wall of the holder, and each of which has the ends thereof integrally affixed to the top wall in diametrically opposite positions so as to span the opening, with one arm being rotatably displaced 90° with respect to the other arm. The two arms also are integrally affixed together at the mid sections thereof effectively in alignment with the longitudinal axis of the bottle. The arms normally project outwardly above the top wall and form the hanger which is usable to support the intravenous bottle to which the holder is affixed in an inverted position. During shipment or storage, however, with the intravenous bottle in its upright position and seated on the support surface formed by the top wall of the holder, the arms are forcibly and automatically coiled and pushed into the cavity provided between the top wall of the holder and the bottom of the bottle. When the bottle is lifted, the arms automatically pop out to form the hanger, as a result of the elastic memory of the arms.

The invention will be easily understood when the following detailed description is read in conjunction with the attached drawings.

BRIEF DESCRIPTION OF THE DRAWINGS

FIG. 1 is a perspective view of the holder and bottle in an inverted hanging position;

FIG. 2 is a bottom plan view of the holder;

FIG. 3 is a sectional view taken substantially along lines 3—3 of FIG. 2, with the sectionalized view of the hanger affixed to a bottle; and FIG. 4 is a partial side plan view, with the hanger sectionalized, to illustrate the manner in which the hanger is retained within the cavity between the top wall of the hanger and the bottom wall of the bottle.

DETAILED DESCRIPTION OF THE PREFERRED EMBODIMENT

In FIG. 1, a hanger 12 exemplary of the invention is illustrated affixed to a bottle 10 which may be, for example, an intravenous bottle. The holder 12 has a hanger portion 14 for suspending the bottle 10 in an inverted position from a hook 16 or the like.

The holder 12 is integrally molded of a plastic material having an elastic memory, preferably low density polyethylene or comparable material. As can be best seen in FIGS. 2-4, the holder 12 includes a top wall 18 which has an opening 20 formed in it. Affixed to the top wall 18 are two generally S-shaped arms 22 and 24, each of which is substantially longer in length than the diameter of the opening 20 in the top wall 18, and each of which is substantially longer in length than the diameter of the opening 20 in the top wall 18, and each of which has the ends thereof integrally affixed to the top wall in diametrically opposed positions so as to span the opening. The one arm 22 is angularly displaced 90° with respect to the other arm 24. The two arms 22 and 24 also are integrally affixed together at the mid sections thereof effectively in alignment with the longitudinal axis of the bottle.

The holder 12 also has a skirt portion 26 which depends from the top wall 18. The diameter of the skirt portion 26 substantially corresponds to the diameter of the bottle 10 so that the holder 12 can be at least frictionally affixed to the bottle 10. However, in most cases, the bottle 10 is provided with an annular recess 30 which is spaced from its bottom 34, and the skirt portion 26 of the holder 12 preferably and advantageously is provided with an annular bead 28 which is proportioned to seat within this annular recess 30 to affix the holder 12 to the bottle 10. It may be further noted that the length of the skirt portion 26 and the location of the annular bead 28 are such that a cavity 32 is provided between the bottom wall 34 of the bottle 10 and the top wall 18 of the holder 12 when the holder 12 is affixed to the bottle 10, for reasons set forth more specifically below.

The holder 12 is molded, generally as shown in FIG. 3, with the arms 22 and 24 projecting upwardly above the top wall 18 and forming a hanger which is usable to support the intravenous bottle 10 to which the holder 12 is affixed in an inverted position. During shipment or storage, however, with the intravenous bottle 10 in its upright position, as illustrated in FIG. 4, and seated on the support surface formed by the top wall 18 of the holder 12, the weight of the bottle 10 and its contents forcibly urge the arms 22 and 24 into the cavity 32 provided between the top wall of the holder 12 and the bottom 34 of the bottle 10. It may be noted that the shape of the arms 22 and 24 is such that the arms automatically coil as they are urged into the cavity 32. When the bottle 10 is lifted, the arms 22 and 24 automatically uncoil, as a result of the elastic memory of the arms, and pop out of the cavity 32 to form the hanger 12.

Accordingly, during shipment or storage, the hanger portion 14 of the holder 12 is automatically recessed into storage in the cavity 32. During use, however, as soon as the bottle 10 is lifted, the hanger portion 14 automatically pops into position for use as a hanger, for hanging the bottle 10 in an inverted position. Further still, when the bottle 10 is in its suspended feeding position, the bottle will not tilt or wobble due to the unique hang web configuration of the hanger portion 14. Therefore, as the solution in the bottle is gradually administered, a constant solution level is maintained, thereby reducing the risk of introducing air in the solution being administered to the patient.

It will be apparent to those skilled in the art that many variations and modifications of the present invention can be made. Such variations and modifications are clearly within the ambit of the appended claims.

We claim:

1. A bottle holder molded of a thermoplastic material having an elastic memory and comprising:
   a top wall having an opening therein;
   a hanger integral with said top wall and spanning said opening;
   an annular skirt integral with said top wall and depending from one side thereof for removably affixing said holder to said bottle with said top wall of said holder spaced from the bottom of said bottle so as to provide an open cavity between said top wall of said holder and said bottom of said bottle for receiving therein said hanger;
   said hanger being forcibly urged into said cavity when said holder is attached to a bottle and the bottle is in an upright position, the elastic memory of said hanger causing said hanger to snap-out of said cavity to an operable position to permit said bottle to be hung in an inverted position when said bottle is lifted and inverted;
   thereby permitting said bottle to be hung in an inverted position by said hanger simply by lifting and inverting said bottle.

2. The bottle holder of claim 1, wherein said hanger comprises a plurality of generally S-shaped arms, each of which is substantially longer in length than the diameter of said opening in said top wall, the opposite ends of said arms being integrally formed with said top wall with said arms spanning said opening, each of said arms further being angularly displaced with respect to one another and molded to normally project outwardly above said top wall, said arms being forcibly urged into said cavity when said holder is attached to a bottle and the bottle is in an upright position, the elastic memory of said arms automatically ejecting said arms from said cavity to form said hanger when said bottle is lifted.

3. The bottle holder of claim 2, wherein said hanger comprises a pair of generally S-shaped arms, one of which is angularly displaced 90° with respect to the other.

4. The bottle holder of claim 1, further comprising an annular bead on the interior peripheral surface of said skirt serving as a snap-ring to removably affix said bottle holder to a bottle.

5. The bottle holder of claim 1, wherein said bottle holder is of a low density polyethylene.

6. The bottle holder of claim 4, in combination with an intravenous feed bottle, said bottle having an annular recess formed in the side wall thereof adjacent its bottom for receiving therein said annular bead.

7. The bottle holder of claim 6, wherein the length of said skirt and the position of said annular bead are such as to provide said cavity between said top wall of said holder and the bottom of said bottle when said annular bead is disposed within said annular recess in said bottle.

* * * * *